United States Patent
Coffey et al.

(10) Patent No.: US 12,102,320 B2
(45) Date of Patent: *Oct. 1, 2024

(54) SMALL DIAMETER FIBER BRAID WITH CENTRAL CORE MEMBER

(71) Applicant: KURARAY CO., LTD., Kurashiki (JP)

(72) Inventors: Patrick Coffey, Houston, TX (US); Forrest Sloan, Houston, TX (US)

(73) Assignee: KURARAY CO., LTD., Kurashiki (JP)

( * ) Notice: Subject to any disclaimer, the term of this patent is extended or adjusted under 35 U.S.C. 154(b) by 98 days.

This patent is subject to a terminal disclaimer.

(21) Appl. No.: 17/546,139

(22) Filed: Dec. 9, 2021

(65) Prior Publication Data

US 2022/0167976 A1 Jun. 2, 2022

Related U.S. Application Data

(63) Continuation of application No. 16/250,586, filed on Jan. 17, 2019, now Pat. No. 11,229,432.
(Continued)

(51) Int. Cl.
*A61B 17/06* (2006.01)
*A61L 17/04* (2006.01)
(Continued)

(52) U.S. Cl.
CPC ........ *A61B 17/06166* (2013.01); *A61L 17/04* (2013.01); *A61L 17/145* (2013.01);
(Continued)

(58) Field of Classification Search
CPC .... A61B 17/06166; A61B 2017/06185; D07B 1/04; D07B 2201/102; D07B 2201/1906; D10B 2509/04

See application file for complete search history.

(56) References Cited

U.S. PATENT DOCUMENTS 3,035,476 A * 5/1962 Fogden .................. D04C 1/00
　　　　　　　　　　　　　　　　　　　　　87/9
4,201,216 A 　　5/1980 Mattei
(Continued)

FOREIGN PATENT DOCUMENTS

CN 　　102869388 A 　　1/2013
CN 　　104135949 A 　　11/2014
(Continued)

OTHER PUBLICATIONS

International Search Report and Written Opinion issued on Apr. 26, 2019 in PCT/US2019/013962, 17 pages.
(Continued)

*Primary Examiner* — Alexander J Orkin
(74) *Attorney, Agent, or Firm* — Element IP, PLC (57) ABSTRACT

A cord comprises a braided sheath of strands having an outer surface, an inner surface, and a central hollow portion defined by the inner surface and having a volume and a core within the central hollow portion of the tubular braided sheath, such that when the cord is in a relaxed state the tubular braided sheath has a cylindrical shape and a relaxed volume of the central hollow portion wherein the core does not fill the relaxed volume of the central hollow portion of the tubular braided sheath; when the cord is in a longitudinal tensioned state, the tubular braided sheath elongates under the longitudinal tension such that a tensioned volume of at least a part of the central hollow portion of the tubular braided sheath is less than the relaxed volume; and the inner surface of the tubular braided sheath of tensioned volume contacts and cinches a surface of the core.

19 Claims, 4 Drawing Sheets

Related U.S. Application Data (60) Provisional application No. 62/620,801, filed on Jan. 23, 2018.

(51) Int. Cl.
*A61L 17/14* (2006.01)
*D04C 1/12* (2006.01)
*D07B 1/02* (2006.01)
*D07B 1/04* (2006.01)
*A61B 17/00* (2006.01)
*D02G 3/44* (2006.01)

(52) U.S. Cl.
CPC ............. *D04C 1/12* (2013.01); *D07B 1/025* (2013.01); *D07B 1/04* (2013.01); *A61B 2017/00526* (2013.01); *A61B 2017/06185* (2013.01); *D02G 3/448* (2013.01); *D07B 2201/102* (2013.01); *D07B 2201/1024* (2013.01); *D07B 2201/1096* (2013.01); *D07B 2201/2055* (2013.01); *D07B 2201/2068* (2013.01); *D07B 2201/209* (2013.01); *D07B 2205/2014* (2013.01); *D07B 2205/2028* (2013.01); *D07B 2205/2042* (2013.01); *D07B 2205/2096* (2013.01); *D07B 2205/3017* (2013.01); *D07B 2401/205* (2013.01); *D10B 2509/04* (2013.01)

(56) References Cited

U.S. PATENT DOCUMENTS

| | | |
|---|---|---|
| 4,510,934 A | 4/1985 | Batra |
| 4,946,467 A | 8/1990 | Ohi et al. |
| 5,217,495 A | 6/1993 | Kaplan |
| 6,045,571 A | 4/2000 | Hill |
| 6,296,659 B1 * | 10/2001 | Foerster ............ A61B 17/0469 623/13.13 |
| 11,229,432 B2 * | 1/2022 | Coffey ................... A61L 17/04 |
| 2004/0267316 A1 | 12/2004 | Powell |
| 2005/0119696 A1 | 6/2005 | Walters |
| 2005/0149119 A1 | 7/2005 | Koyfman |
| 2008/0281355 A1 | 11/2008 | Mayer |
| 2009/0048628 A1 | 2/2009 | Marissen |
| 2010/0137679 A1 | 6/2010 | Lashinski |
| 2013/0231700 A1 | 9/2013 | Gedet |
| 2013/0255045 A1 | 10/2013 | Gonzalez |
| 2023/0149015 A1 * | 5/2023 | Coffey .................. D07B 1/025 606/231 |

FOREIGN PATENT DOCUMENTS

| | | |
|---|---|---|
| EP | 0485986 A1 | 5/1992 |
| JP | 4850413 B2 | 1/2012 |
| JP | 2015511502 A | 4/2015 |
| WO | WO-2011135082 A1 | 11/2011 |
| WO | WO-2013130547 A1 | 9/2013 |
| WO | WO-2014110599 A1 | 7/2014 |
| WO | WO-2015161253 A1 | 10/2015 |

OTHER PUBLICATIONS

Office Action issued Oct. 19, 2023 in Canadian Patent Application No. 3,087,575, 5 pages.

Office Action issued Feb. 29, 2024 in corresponding Korean Patent Application No. 10-2020-7024146 (with English summary and translation), 13 pages.

* cited by examiner

SMALL DIAMETER FIBER BRAID WITH CENTRAL CORE MEMBER

CROSS REFERENCE TO RELATED APPLICATION

This application claims priority under 35 U.S.C. § 119 from U.S. Provisional Application Ser. No. 62/620,801 (filed 23 Jan. 2018), the disclosure of which is incorporated by reference herein for all purposes as if fully set forth.

TECHNICAL FIELD

The present invention is directed to small diameter tensile load managed braided cords having increased overall strength and dimensional stability over conventionally known cords of the same diameter. The cords are suitable for utility where small diameter and high strength are required.

BACKGROUND OF THE INVENTION

Braided cords having a central core structure are conventionally available for utility in a wide variety of applications. In general terms, in each of the known structures the braided outer sheath serves to protect the inner core structure from for example, abrasion wear and environmental stress. The central core structure whether a single component or a plurality of threads which may be intertwined, braided and/or further twisted contributes to the strength and stiffness of the cord. Thus, conventionally, the strength of the cord may be increased by modification of the size and construction of the core. In applications such as large diameter rope increasing the diameter of the core and thus the rope generally does not adversely affect utility value. However, in applications requiring small diameter, less than 3 mm, and high tenacity, increasing strength by increasing the diameter of the cord is not a desirable approach.

Conventional ropes of double braid construction where the cover and central core are each designed to each carry a significant portion of a tensioned load are known. These ropes which are available in diameters as small as about 0.25 inch (about 6 mm) are typically made with lower modulus fibers such as nylon or polyester. With such lower modulus materials, constructing a core sheath structure cord where longitudinal stress load is proportionately shared is possible by proper adjustment of the core and sheath strand twist, braid patterns and lay angles. However, when constructing a cord with high strength, high modulus materials such as, for example, high molecular weight polyethylene (HMPE) or liquid crystal polymer (LCP), core and sheath geometries cannot easily balance the longitudinal load, and consequently, in conventional high-tenacity cords the core is responsible for carrying essentially all of the longitudinal stress.

The tensile loads carried by conventional small diameter braided cords may not be evenly distributed between the braided sheath and the central core member. As a consequence, when these cords are stretched, the braided sheath and the core respond differently to the application of the tensile forces. The sheath will respond to the forces independently of the central core member, causing the central threads to move longitudinally relative to the surrounding sheath. The core member, especially if constructed of threads may also flatten and redistribute themselves within the sheath instead of maintaining a rounded cross-sectional shape.

Thus, in many very fine cords (diameter less than about 3 mm) of fine braids, there may normally be no core component and the fine cord may be constructed as a hollow braid, primarily for simplicity of construction. A significant disadvantage of this approach is that to incrementally increase the load capacity of such a small diameter cord, a small quantity of fiber may be added to each of the braided elements. Adding to each element maintains the overall torque balance of the structure. Thus in a braided cord structure of 12 strands, each strand would be increased in size to effect an increase of strength of the cord. When dealing with very fine cords, i.e., cords of less than 3 mm diameter, in this manner, the cord maker must consider the available incremental fiber deniers. For example, in consideration of a 12-strand braided cord where each strand is a 100 denier LCP fiber, the next increment of strength increase available would be where each strand was constructed of two 100 denier LCP fibers. However, this increase in total fiber count also results in overall cord diameter increase of about 1.4 times the original diameter.

Therefore, it would be advantageous to have a structure for very fine and ultrafine cords (1 mm or less in external diameter) which are designed for tensile load management such that the full tensile stress is proportionately assumed by all components of the cord such that overall strength is increased with little or no corresponding increase in diameter, wherein tensile forces are more uniformly distributed between the core and sheath components, so that the entire structure of the cord will respond in unison to the tensile forces preferably without distortion of the normal shape of the cord. Moreover, with such tensile load managed structure it should be possible to obtain a cord of a set diameter having increased stability and strength over conventional cords of the same diameter.

Thus an object of the present invention is to design a cord structure of external diameter less than 6 mm using high modulus fibers wherein the design leads to a tensile load managed structure such that tensile load is proportionately shared by all components of the cord.

SUMMARY OF THE INVENTION

These and other objects are achieved by the present invention, the first embodiment of which provides a cord comprising:

a tubular braided sheath of strands having an outer surface, an inner surface, and a central hollow portion defined by the inner surface and having a volume; and a core within the central hollow portion of the tubular braided sheath;

wherein:

the tubular braided sheath comprises strands each having a tensile strength of about 8 cN/dtex or more;

when the cord is in a relaxed state, the tubular braided sheath has a substantially cylindrical shape having an outer diameter of from about 20 μm to about 5 mm and a relaxed volume of the central hollow portion wherein the core does not fill the relaxed volume of the central hollow portion of the tubular braided sheath; and when the cord is in a longitudinal tensioned state, the tubular braided sheath elongates under the longitudinal tension such that a tensioned volume of at least a part of the central hollow portion of the tubular braided sheath is less than the relaxed volume; and the inner surface of the tubular braided sheath of tensioned volume contacts and cinches a surface of the core such that slippage between the core and the tubular braided sheath is reduced.

In an aspect of the first embodiment, a pick count of the braid of the tubular braided sheath in the relaxed state is from 30 to 3000 filament unit crossovers per meter and a pick count of the tubular braided sheath in a longitudinal tensioned state is reduced in comparison to a pick count in the relaxed state.

In another aspect of the first embodiment, the core component occupies greater than about 95% of the volume of the central hollow portion of the tubular braided sheath in the relaxed state.

In further aspects of the first embodiment, each strand of the tubular braided sheath may be a twisted or untwisted monofilament, or a twisted or untwisted multifilament, or the tubular braided sheath is a combination of strands, wherein each strand is individually or a twisted or untwisted monofilament or multifilament.

In another aspect of the first embodiment, the strands of the tubular braided sheath may be filaments selected from the group consisting of a liquid crystalline polyester filament, an aramid filament, co-polymer aramid filament, a polyether ether ketone filament, a poly(p-phenylene benzobisoxazole) filament, an ultra-high molecular weight polyethylene filament, a high modulus polyethylene filament, a polypropylene filament, a polyethylene terephthalate filament, a polyamide filament, a polyhydroquinone diimidazopyridine filament, a high-strength polyvinyl alcohol filament and combinations thereof.

In additional aspects of the first embodiment, a strand (end) count of the tubular braided sheath may be from 4 to 24.

In a further additional aspects the core component may be a twisted or untwisted monofilament or multifilament structure; and/or the one or more filaments may be selected from the group consisting of a liquid crystalline polyester filament, an aramid filament, co-polymer aramid filament, a polyether ether ketone filament, a poly(p-phenylene benzobisoxazole) filament, an ultra-high molecular weight polyethylene filament, a high modulus polyethylene filament, a polypropylene filament, a polyethylene terephthalate filament, a polyamide filament, a high-strength polyvinyl alcohol filament, polyhydroquinone diimidazopyridine filament (PIPD) and combinations thereof. In another aspect, the core is a combination of strands, wherein each strand is individually a twisted or untwisted monofilament or multifilament. In a further additional aspect the core is twisted and the twist structure comprises from greater than 0 up to 1600 turns per meter.

In another aspect of the first embodiment a mass ratio of a mass of the tubular braided sheath to a mass of the core per unit length of the cord is from about 95/5 to about 50/50.

In another further aspect of the first embodiment the outer diameter of the tubular braided sheath when the cord is in a relaxed state, is from about 20 μm to about 5 mm.

In another further aspect of the first embodiment, the linear density of the cord is from about 30 to about 5000 denier or even from about 50 to about 5000 denier.

In an additional further aspect of the first embodiment, a braid angle of the tubular braided sheath is from about 5° to about 85° in the relaxed state and the braid angle is decreased in the longitudinal tensioned state.

In a second embodiment the present invention provides a cord according to the first embodiment and all the above aspects, wherein at least one of the core and the tubular braided sheath comprises a filament, fiber or strand having a coating of a cross-linked silicone polymer, or a non-cross-linked silicone polymer or a long chain fatty acid.

In another embodiment, the present invention relates to a medical thread or suture comprising a cord according to the embodiments described herein, having an outer diameter of from about 0.04 mm to about 0.7 mm.

The forgoing description is intended to provide a general introduction and summary of the present invention and is not intended to be limiting in its disclosure unless otherwise explicitly stated. The presently preferred embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

In the context of the present description, all publications, patent applications, patents and other references mentioned herein, if not otherwise indicated, are explicitly incorporated by reference herein in their entirety for all purposes as if fully set forth.

Unless otherwise defined, all technical and scientific terms used herein have the same meaning as commonly understood by one of ordinary skill in the art to which this disclosure belongs. In case of conflict, the present specification, including definitions, will control.

Except where expressly noted, trademarks are shown in upper case.

Unless stated otherwise, all percentages, parts, ratios, etc., are by weight.

When an amount, concentration, or other value or parameter is given as a range, or a list of upper and lower values, this is to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

When the term "about" is used, it is used to mean a certain effect or result can be obtained within a certain tolerance, and the skilled person knows how to obtain the tolerance.

When the term "about" is used in describing a value or an end-point of a range, the disclosure should be understood to include the specific value or end-point referred to.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus.

The transitional phrase "consisting of" excludes any element, step, or ingredient not specified in the claim, closing the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Optional additives as defined herein, at a level that is appropriate for such additives, and minor impurities are not excluded from a composition by the term "consisting essentially of".

Further, unless expressly stated to the contrary, "or" and "and/or" refers to an inclusive and not to an exclusive. For example, a condition A or B, or A and/or B, is satisfied by any one of the following: A is true (or present) and B is false (or not present), A is false (or not present) and B is true (or present), and both A and B are true (or present).

The use of "a" or "an" to describe the various elements and components herein is merely for convenience and to give a general sense of the disclosure. This description should be read to include one or at least one and the singular also includes the plural unless it is obvious that it is meant otherwise.

The term "predominant portion" or "predominantly", as used herein, unless otherwise defined herein, means greater than 50% of the referenced material. If not specified, the percent is on a molar basis when reference is made to a molecule (such as hydrogen and ethylene), and otherwise is on a mass or weight basis (such as for additive content).

The term "substantial portion" or "substantially", as used herein, unless otherwise defined, means all or almost all or the vast majority, as would be understood by the person of ordinary skill in the context used. It is intended to take into account some reasonable variance from 100% that would ordinarily occur in industrial-scale or commercial-scale situations.

The term "depleted" or "reduced" is synonymous with reduced from originally present. For example, removing a substantial portion of a material from a stream would produce a material-depleted stream that is substantially depleted of that material. Conversely, the term "enriched" or "increased" is synonymous with greater than originally present.

As used herein, the term "copolymer" refers to polymers comprising copolymerized units resulting from copolymerization of two or more comonomers. In this connection, a copolymer may be described herein with reference to its constituent comonomers or to the amounts of its constituent comonomers, for example "a copolymer comprising ethylene and 15 weight % of a comonomer", or a similar description. Such a description may be considered informal in that it does not refer to the comonomers as copolymerized units; in that it does not include a conventional nomenclature for the copolymer, for example International Union of Pure and Applied Chemistry (IUPAC) nomenclature; in that it does not use product-by-process terminology; or for another reason. As used herein, however, a description of a copolymer with reference to its constituent comonomers or to the amounts of its constituent comonomers means that the copolymer contains copolymerized units (in the specified amounts when specified) of the specified comonomers. It follows as a corollary that a copolymer is not the product of a reaction mixture containing given comonomers in given amounts, unless expressly stated in limited circumstances to be such.

Throughout the present description, unless otherwise defined and described, technical terms and methods employed to determine associated measurement values are in accordance with the description of ASTM D885M-94, Standard Test Methods for Tire Cords, Tire Cord Fabrics, and Industrial Filament Yarns Made From Man-made Organic-base Fibers [Metric] published February, 1995.

For convenience, many elements of the present invention are discussed separately, lists of options may be provided and numerical values may be in ranges; however, for the purposes of the present disclosure, that should not be considered as a limitation on the scope of the disclosure or support of the present disclosure for any claim of any combination of any such separate components, list items or ranges. Unless stated otherwise, each and every combination possible with the present disclosure should be considered as explicitly disclosed for all purposes.

Although methods and materials similar or equivalent to those described herein can be used in the practice or testing of the present disclosure, suitable methods and materials are described herein. The materials, methods, and examples herein are thus illustrative only and, except as specifically stated, are not intended to be limiting.

As described in the background discussion, cord structures having an outer sheath of braided strands and a core component within the sheath are conventionally known and applied to diverse utilities bridging from common rope to textile thread. However, for specialized applications requiring fine and ultrafine cords achieving a cord of minimal diameter while providing a product of high strength and stability is the subject of ongoing study. As previously described, increasing strength of hollow braided structures results in significant increase of the diameter.

Typically, the function of the sheath is to provide protection to the core component while the core carries the tension load and is responsible for providing strength to the cord.

However, in applications where high strength and stability coupled with small outside diameter, less than for example, 1 mm, is required, the inventors have investigated designs which may provide tensile load management wherein tensile force stress is shared by all components of the cord and have considered that having a sheath structure which contributes to and/or proportionately assumes tensioned stress applied to the cord would provide a cord wherein the entire diameter contributes to strength and stability in all aspects and thereby provides a cord having greater strength and dimensional stability in comparison to conventional core sheath cords where the sheath serves mainly as a protective layer on the core member.

The present inventors have discerned that with a specific structural arrangement of a core sheath, fine diameter cord containing a high modulus fiber where tensile forces are more uniformly distributed between the core and sheath components, so that the entire structure of the cord will respond in unison to the tensile forces preferably without distortion of the normal shape of the cord may be obtained. With such structure it should be possible to obtain a cord of a set diameter having increased stability and strength over conventional cords of the same diameter. Unlike, a hollow braid fine or ultrafine cord, the inventors have reasoned that providing a core structure would permit incremental increase in strength by increasing fiber count while having minimal effect on diameter in comparison to increase of fiber count in the sheath braid as previously described. The inventors have reasoned that more fine increments of strength increase may be obtained, for example with 100 denier fiber LCP if 1×100d increments are progressively added to the core element rather than the sheath braid. Correspondingly, a core component having a braid and/or twist and the sheath braid angle may be matched to distribute stress load evenly between the core and the sheath. For applications requiring a cord having a diameter of 5 mm or less which has a combination of high tensile strength and low creep a design wherein tensile load is managed to be proportionately distributed to the core and sheath would be advantageous.

Thus in a first embodiment, the present invention provides a cord comprising:

a tubular braided sheath of strands having an outer surface, an inner surface, and a central hollow portion defined by the inner surface and having a volume; and a core within the central hollow portion of the tubular braided sheath;

wherein:

the tubular braided sheath comprises strands each having a tensile strength of about 8 cN/dtex or more;

when the cord is in a relaxed state, the tubular braided sheath has a substantially cylindrical shape having an outer diameter of from about 20 μm to about 5 mm and a relaxed volume of the central hollow portion wherein the core does not fill the relaxed volume of the central hollow portion of the tubular braided sheath; and when the cord is in a longitudinal tensioned state, the tubular braided sheath elongates under the longitudinal tension such that a tensioned volume of at least a part of the central hollow portion of the tubular braided sheath is less than the relaxed volume; and the inner surface of the tubular braided sheath of tensioned volume contacts and cinches a surface of the core such that slippage between the core and the tubular braided sheath is reduced.

In one embodiment of the cord, when in a relaxed state, the relationship between the sheath and core components of the cord conforms to the equation (I)

$$c/10 \le p/t \le (1.2 \cdot c) \qquad (I)$$

wherein c is the strand count of the tubular braided sheath, p is the pick count per meter in the sheath, and t is the twist level of the core in turns per meter.

Desirably, a linear density of the sheath substantially matches a linear density of the core.

Figure 1:
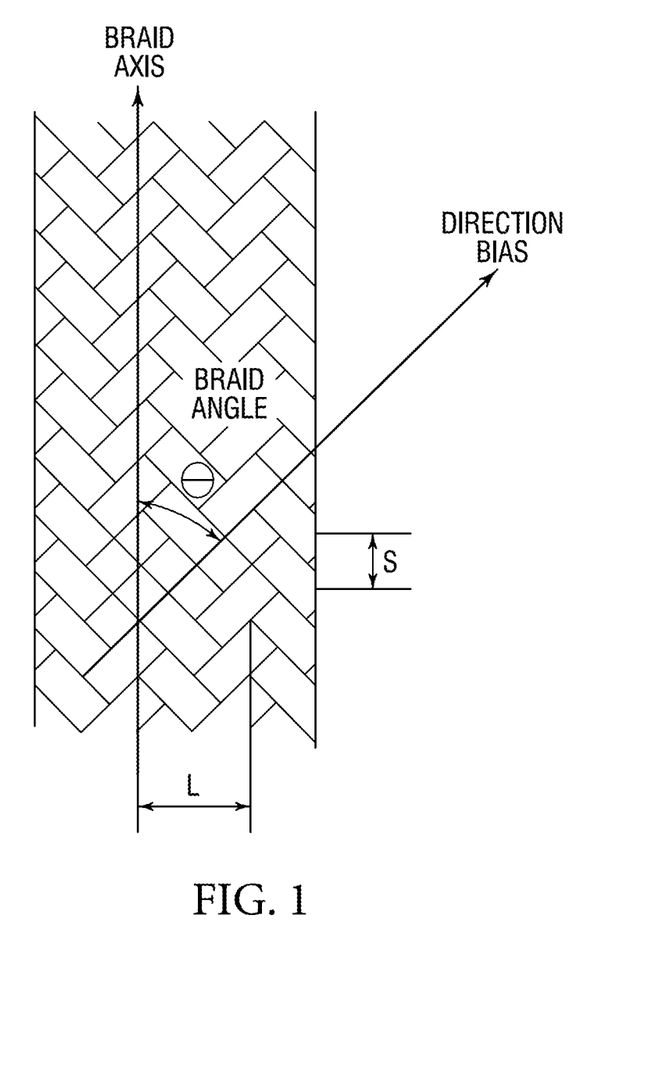
FIG. 1 shows a schematic diagram of a braided structure.

Tubular braiding about a core element is conventionally known and tubular braiding units are commercially available. A simple tubular braid sheath may be formed on a core component by mechanically crossing a number of strands of a material diagonally in such a way that each group of strands pass alternately over and under a group of strands laid in the opposite direction. A general diagram of a braided structure is shown in FIG. 1 where a longitudinal braid axis runs parallel to the direction of the cord and a line of direction parallel to a given braided strand defines a braid angle of the braid structure.

In addition to braid angle, a braid may be characterized by a pick number which is defined as the number of stitches or S units encountered per unit length along the longitudinal braid axis. Further, in addition to the pick count regarding the longitudinal direction of the braid, the braid may also be characterized by the line number which defines the number of repeat units per unit dimension along a line perpendicular to the braid axis. Braid angle, pick number and line number may be determined by observation of the braid under a microscope.

Figure 2:
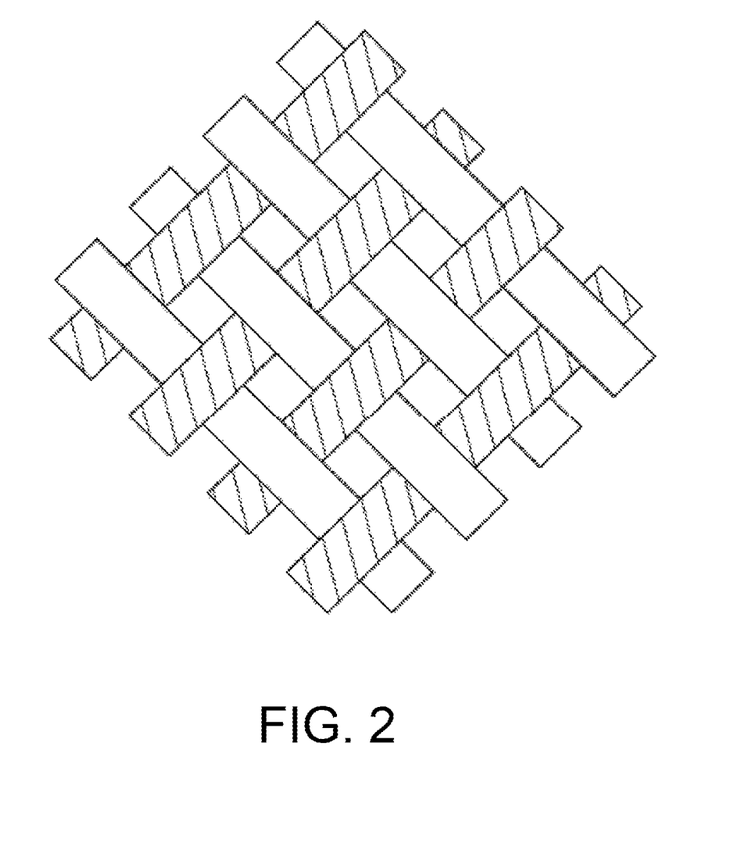
FIG. 2 shows a schematic representation of a 1×1 braid pattern.
Figure 3:
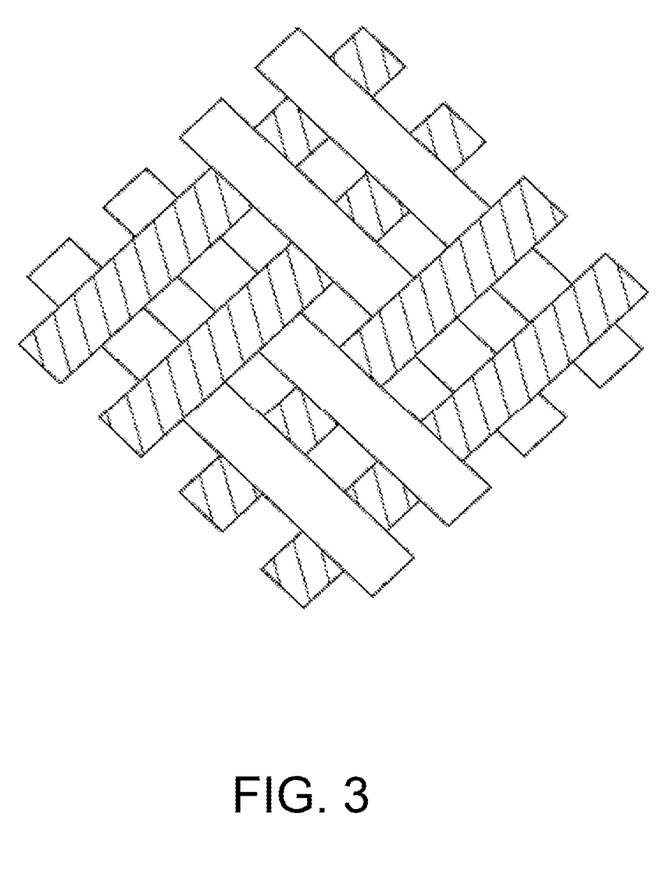
FIG. 3 shows a schematic representation of a 2×1 braid pattern.
Figure 4A:
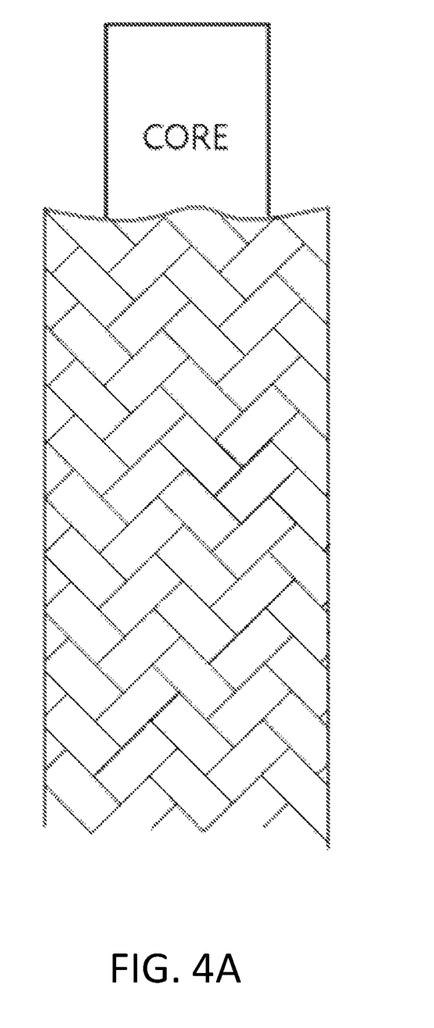
FIG. 4A shows a schematic representation of a core within the central hollow portion of a tubular braided sheath, in a relaxed state.
Figure 4B:
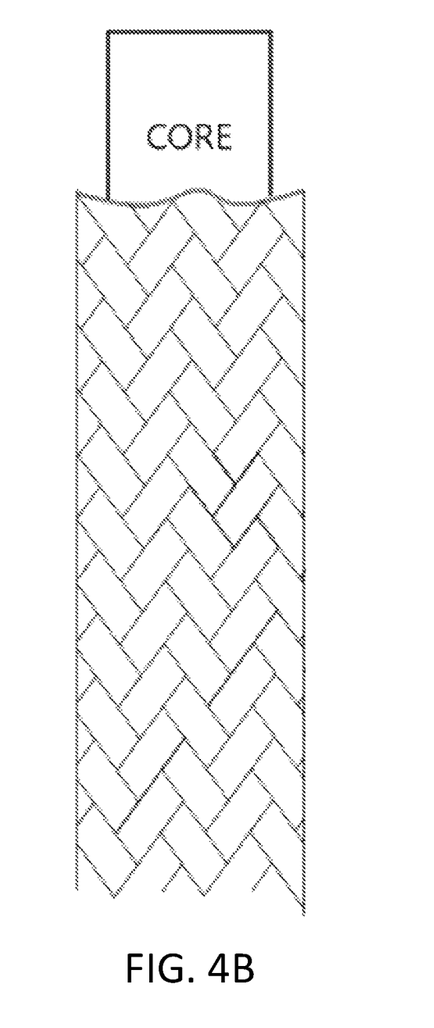
FIG. 4B shows a schematic representation of a core within the central hollow portion of a tubular braided sheath, in a longitudinal tensioned state, where the tubular braided sheath elongates under the longitudinal tension such that a volume of at least a part of the central hollow portion of the tubular braided sheath in the tensioned state is less than the volume in the relaxed state.

The actual braid pattern may be varied according to the pattern of interlacing. Common patterns include plain, twill and panama weave and these are known to the person of skill in the art. Additionally, different braid structure may be categorized by the number of strands in side by side identical weave. Common braid patterns may be exemplified by but are not limited to a 1×1 pattern (FIG. 2) and a 2×1 pattern (FIG. 3).

Throughout the embodiments of this invention, the twist, braid pattern, and lay angle of the strands of the central core and tubular braided sheath are designed to balance the tensile loads between the core and sheath.

Braiding equipment is commercially available and units of differing capabilities may be obtained. In the embodiments described herein the braid may be produced on STEEGER (Steeger USA, Inman, South Carolina USA) and/or HERZOG (Herzog GmbH, Oldenburg, Germany) braiding equipment that is designed for the braiding of finer deniers. However, the equipment is not limited to these units. Essential to the sheath core design is that the braiding equipment be equipped with the ability to braid around a central core. STEEGER is well known to those skilled in the art as a machine with sheath core capability. According to the embodiments herein the minimum number of carriers to produce the braid is three (3). An upper limit of carriers is not limited and may be determined according to braid parameters and design.

In highly specialized aspects of the invention the core component surface may be corona or plasma treated prior to application of the tubular braided sheath. Such treatment may create surface imperfections or modifications which enhance the contact surface interaction between the core component and inner surface of the tubular braided sheath when in the longitudinal tensioned state, further enhancing the cinch effect and enhancing the equalization of the load sharing between the core component and sheath.

The invention according the present embodiments and aspects may be obtained by application of any of known patterns and characteristics as long as the elements disclosed are present.

According to the embodiments of this invention the braided tubular sheath may be formed about a core component such that the volume of the central hollow portion of the tubular braided sheath is not fully occupied by the core component when the tubular braided sheath is not under a longitudinal tension and is in a relaxed state. In the relaxed state the braid may be defined at least by an outer diameter, a braid angle and a pick count. According to the first embodiment the outer diameter of the braid (and thus also the cord) is from about 20 μm to about 5 mm, or to about 3 mm, or to about 1 mm.

Tubular braided sheaths may be prepared with an even number of strands and cord structures according to the present invention may have from 4 to 24, or to 18, or to 12 strands (ends).

A tensile strength of each strand may be at least about 8 cN/dtex, or at least about 15 cN/dtex, or at least about 22 cN/dtex, and typically to about 30 cN/dtex. Higher tensile strength strands may be used as long as the strand has sufficient flexibility to be handled in a braiding device. If the strand tensile strength is less than about 8 cN/dtex, the strands may not have sufficient strength to cinch to the core when subjected to a longitudinal tensioned state as described in the following paragraphs.

As described above, when the cord is in a relaxed state, there is open volume present in the hollow portion of the tubular braided sheath not occupied by the core member. In the relaxed state the braid angle of the tubular braided sheath may be from about 5° to about 85°. However, when a longitudinal tension is applied to the cord, the applied tension results in a longitudinal tensioned state wherein the braided structure is elongated such that the braid angle is decreased and the pick count is decreased. Moreover, due to the elongation the diameter of the tubular braided sheath (outside and inside) constricts such that at least portions of the inner surface of the tubular braided sheath contact and cinch the core member.

Due to the effect of the cinching structure obtained under the longitudinal tension and the load balance achieved by proper core and sheath design, tensile load management results in that the core component and braided tubular sheath function collaterally to provide tensile strength to the cord.

As will be understood by one of skill in the art the cinch effect and tensile strength achieved according to the first embodiment may be tailored by selection of braid pattern, strand count, strand construction, strand twist, braid angle and pick count of the braid along with the core construction and twist, in the relaxed state. The effect of these variables and others familiar to one of skill in braiding technology may be determined through routine experimentation and/or structural analysis.

The strand components of the tubular braided sheath may be of a twisted or untwisted monofilament structure, a twisted or untwisted multifilament structure or a combination of twisted or untwisted monofilaments and twisted or untwisted multifilaments. The monofilament may be twisted and multifilament structure may be braided and/or twisted. In some aspects where a twist structure is present, the twist structure may include a twist count of up to 1600 tpm.

The individual filaments may vary in weight from about 0.2, or from about 0.4, or from about 0.6, to about 10, or to about 8.0, or to about 6.0 denier. One of ordinary skill in the relevant art recognizes that the filament denier selected will vary with chemical composition of the filament and intended end use of the cord.

In an aspect of these embodiments, the strands of the sheath braid may be identical in size, structure and composition or the strands may differ in any or all of size, structure and composition. Thus the sheath may be constructed of strands of differing denier, braid or twist such that a strong grip or cinch of the core may be obtained when the cord is in a longitudinal tensioned state. Further a braid may contain strands of differing chemical composition. Such structure may be designed to further increase strength and torque properties of the cord through experimental design tools understood by one of skill in the art.

The chemical composition of the strands (or filaments) of the tubular braided sheath may be of any high performance polymer known to provide a combination of high tensile strength, high tenacity and low creep and may be selected from but is not restricted to filaments selected from the group consisting of a liquid crystalline polyester filament, an aramid filament, co-polymer aramid filament, a polyether ether ketone filament, a poly(p-phenylene benzobisoxazole) (PBO) filament, an ultra-high molecular weight polyethylene filament, a high modulus polyethylene filament, a polypropylene filament, a polyethylene terephthalate filament, a polyamide filament, a high-strength polyvinyl alcohol filament, a polyhydroquinone diimidazopyridine (PIPD) filament and combinations thereof.

More specifically, the strands preferably comprise, for example, at least one fiber selected from a group consisting of a liquid crystalline polyester fiber, an aramid fiber, a PBO fiber, an ultra-high molecular weight polyethylene fiber, and a high strength polyvinyl alcohol fiber, more preferably at least one fiber selected from a group consisting of a liquid crystalline polyester fiber and an aramid fiber, and particularly preferably a liquid crystalline polyester fiber.

In an embodiment of the present invention, the liquid crystalline polyester fiber may be obtained by melt spinning of a liquid crystalline polyester resin. The spun fiber may be further heat treated to enhance mechanical properties. The liquid crystalline polyester is composed of a repeating polymerized unit, for example, derived from an aromatic diol, an aromatic dicarboxylic acid, or an aromatic hydroxycarboxylic acid. The liquid crystalline polyester may optionally further comprise a polymerized unit derived from an aromatic diamine, an aromatic hydroxyamine, or an aromatic aminocarboxylic acid.

Exemplary polymerized units are shown in Table 1.

TABLE 1

(in which X in the formulas is selected from the following structures)

TABLE 1-continued (in which m = 0 to 2, and Y = a substituent selected from a hydrogen atom, a halogen atom, an alkyl group, an aryl group, an aralkyl group, an alkoxy group, an aryloxy group, and an aralkyloxy group)

The number of Y substituent groups in these formulas ranges is equal to the maximum number of substitutable positions in the ring structure, and each Y independently represents a hydrogen atom, a halogen atom (for example, a fluorine atom, a chlorine atom, a bromine atom, an iodine atom, etc.), an alkyl group (for example, an alkyl group having 1 to 4 carbon atoms such as a methyl group, an ethyl group, an isopropyl group, or a t-butyl group), an alkoxy group (for example, a methoxy group, an ethoxy group, an isopropoxy group, an n-butoxy group, etc.), an aryl group (for example, a phenyl group, a naphthyl group, etc.), an aralkyl group [a benzyl group (a phenylmethyl group), a phenethyl group (a phenylethyl group), etc.], an aryloxy group (for example, a phenoxy group, etc.), or an aralkyloxy group (for example, a benzyloxy group, etc.).

More preferable polymerized units may be the structures shown Table 2, Table 3, and Table 4.

TABLE 2

TABLE 3

(9) Chemical structures (10) Chemical structures (11) Chemical structures (12) Chemical structures (13) Chemical structures (14) Chemical structures

(15) Chemical structures

TABLE 4

(16) Chemical structures (17) Chemical structures

TABLE 4-continued (18)

When the polymerized unit in the formulas is a unit which can represent plural structures, two or more units may be used in combination as polymerized units constituting a polymer.

In the polymerized units of Tables 2, 3, and 4, n is an integer of 1 or 2, and the respective units n=1, n=2 may exist alone or in combination; and $Y_1$ and $Y_2$ each independently may be a hydrogen atom, a halogen atom (for example, a fluorine atom, a chlorine atom, a bromine atom, an iodine atom, etc.), an alkyl group (for example, an alkyl group having 1 to 4 carbon atoms such as a methyl group, an ethyl group, an isopropyl group, or a t-butyl group), an alkoxy group (for example, a methoxy group, an ethoxy group, an isopropoxy group, an n-butoxy group, etc.), an aryl group (for example, a phenyl group, a naphthyl group, etc.), an aralkyl group (a benzyl group (a phenylmethyl group), a phenethyl group (a phenylethyl group), etc.), an aryloxy group (for example, a phenoxy group, etc.), or an aralkyloxy group (for example, a benzyloxy group, etc.). Among these groups, Y is preferably a hydrogen atom, a chlorine atom, a bromine atom, or a methyl group.

Moreover, Z in line (14) of Table 3 may comprise divalent groups represented by the following formulas.

A liquid crystalline polyester may preferably be a combination comprising a naphthalene skeleton as a polymerized unit. Particularly preferably, it comprises both a polymerized unit (A) derived from hydroxybenzoic acid and a polymerized unit (B) derived from hydroxynaphthoic acid. For example, the unit (A) may be of formula (A) and the unit (B) may be of formula (B). From the viewpoint of improving melt moldability, a ratio of the units (A) to the units (B) may be in a range of from 9/1 to 1/1, preferably 7/1 to 1/1, and more preferably 5/1 to 1/1.

The total of the polymerized units (A) and the polymerized units (B) may be, for example, about 65 mol % or more, or about 70 mol % or more, or about 80 mol % or more, based on the total polymerized units. A liquid crystalline polyester comprising about 4 to about 45 mol % of the polymerized unit (B) in the polymer may be particularly preferable.

A melting point of the liquid crystalline polyester may be in a range of from about 250° C., or about 260° C., to about 360° C., or to about 320° C. The melting point as used herein is a main absorption peak temperature which is measured and observed by a differential scanning calorimeter (DSC; "TA3000" manufactured by METTLER Co.) in accordance with the JIS K7121 test method. Specifically, 10 to 20 mg of a sample is used in the above-mentioned DSC apparatus and, after the sample is encapsulated in an aluminum pan, nitrogen is allowed to flow as a carrier gas at a flow rate of 100 cc/minute and an endothermic peak upon heating at a rate of 20° C./minute is measured. When a well-defined peak does not appear at the first run in the DSC measurement depending on the type of the polymer, the temperature is raised to a temperature which is 50° C. higher than an expected flow temperature at a temperature rise rate (or heating rate) of 50° C./minute, followed by complete melting at the same temperature for 3 minutes and further cooling to 50° C. at a temperature drop rate (or cooling rate) of −80° C./minute. Thereafter, the endothermic peak may be measured at a temperature rise rate of 20° C./minute.

Commercially available LCP include VECTRAN® HT BLACK manufactured by KURARAY CO., LTD., VECTRAN® HT manufactured by KURARAY CO., LTD., SIVERAS® manufactured by Toray Industries, Inc., monofilament manufactured by ZEUS and ZXION® manufactured by KB SEIREN, LTD.

The liquid crystalline polyesters may be used alone or in combination.

According to the present invention, "aramid fiber" means a polyamide fiber with high heat resistance and high strength comprising a molecular skeleton composed of an aromatic (benzene) ring.

Aramid fiber may be classified into a para-aramid fiber and a meta-aramid fiber according to a chemical structure thereof.

The "aramid fiber" preferably comprises a para-aramid fiber.

Examples of commercially available aramid fibers include para-aramid fibers, for example, KEVLAR® manufactured by E.I. du Pont de Nemours and Company, HERACRON® from Kolon Industries Inc. and TWARON® and TECHNORA® manufactured by Teijin Limited; and meth-aramid fibers, for example, NOMEX® manufactured by E.I. du Pont de Nemours and Company and CONEX® manufactured by Teijin Limited.

These aramid fibers may be used alone or in combination.

Polyhydroquinone diimidazopyridine (PIPD) filament fibers are based on polymers of the following repeating unit:

This material is conventionally referred to as M5 and is available from DuPont.

Polyparaphenylenebenzobisoxazole (poly(p-phenylene-2,6-benzobisoxazole) (PBO) fibers are commercially available as ZYLON® AS and ZYLON® HM manufactured by TOYOBO CO., LTD.

Ultra-high molecular weight polyethylene fibers according to the present embodiments may have an intrinsic viscosity in a range of from about 5.0, or from about 7.0, or from about 10, to about 30, or to about 28, or to about 24 dL/g. When the intrinsic viscosity of the "ultra-high molecular weight polyethylene fiber" is in a range of from about 5.0 to about 30 dL/g, fibers having good dimensional stability are obtained.

ASTM standards (for example Test Methods D789, D1243, D1601, and D4603, and Practice D3591) that describe dilute solution viscosity procedures for specific polymers, such as nylon, poly(vinyl chloride), polyethylene, and poly(ethylene terephthalate) are available. Generally, the polymer is dissolved in dilute solution and a drop time through a capillary tube versus a control sample is measured at a specific temperature.

A weight average molecular weight of the "ultra-high molecular weight polyethylene fiber" may be from about 700,000, or from about 800,000, or from about 900,000, to about 8,000,000, or to about 7,000,000, or to about 6,000,000. When the weight average molecular weight of the "ultra-high molecular weight polyethylene fiber" is in the range of from about 700,000 to about 8,000,000, having high tensile strength and elastic modulus may be obtained.

It is impossible to easily determine the weight average molecular weight of the "ultra-high molecular weight polyethylene fiber" by a usual GPC method, so that it is possible to determine the weight average molecular weight based on a value of the above mentioned intrinsic viscosity according to the following equation mentioned in "Polymer Handbook Fourth Edition, Chapter 4 (John Wiley, published 1999)".

Weight average molecular weight=$5.365 \times 10^4 \times$(intrinsic viscosity)$^{1.37}$ It is preferred that a repeating unit of the "ultra-high molecular weight polyethylene fiber" is substantially ethylene. However, it may be possible to use, in addition to a homopolymer of ethylene, a copolymer of ethylene with a small amount of another monomer, for example, α-olefin, acrylic acid and derivatives thereof, methacrylic acid and derivatives thereof, and vinylsilane and derivatives thereof. The polyethylene fiber may have a partial crosslinked structure. The polyethylene fiber may also be a blend of a high density polyethylene with an ultra-high molecular weight polyethylene, a blend of a low density polyethylene with an ultra-high molecular weight polyethylene, or a blend of a high density polyethylene, a low density polyethylene with an ultra-high molecular weight polyethylene. The polyethylene fiber may be a combination of two or more ultra-high molecular weight polyethylenes having different weight average molecular weights, or two or more polyethylenes having different molecular weight distributions.

Commercially available "ultra-high molecular weight polyethylene fibers" include DYNEEMA® SK60, DYNEEMA® SK, IZANAS SK60 and IZANAS® SK71 manufactured by TOYOBO CO., LTD.; and SPECTRA FIBER 900® and SPECTRA FIBER 1000 manufactured by Honeywell, Ltd.

These "ultra-high molecular weight polyethylene fibers" can be used alone or in combination.

The core component may be a twisted or untwisted monofilament or a twisted or untwisted multifilament or a combination of twisted or untwisted monofilaments and twisted or untwisted multifilaments. The core component may be a braided structure. The core composition may be of any high performance polymer filament(s) previously described and may be filaments selected from the group consisting of a liquid crystalline polyester filament, an aramid filament, co-polymer aramid filament, a polyether ether ketone filament, a poly(p-phenylene benzobisoxazole) filament, an ultra-high molecular weight polyethylene filament, a high modulus polyethylene filament, a polypropylene filament, a polyethylene terephthalate filament, a polyamide filament, a high-strength polyvinyl alcohol filament and combinations thereof.

The core component filament composition may be selected and structured for specific properties related to the intended end use of the cord.

One of skill recognizes that along with the polymer composition of the core member selected, the weave or braid and/or twist applied to the core member whether monofilament or multifilament, may be adjusted in combination with the tailoring of the tubular braided sheath described above to modify and equalize the load sharing contribution of the core and tubular braided sheath. In this manner the overall tensile strength and dimensional stability of the cord may be increased while maintaining or decreasing the diameter of the cord.

In one specialized embodiment of the present invention the cord may contain a LCP core component and a LCP tubular braided sheath. The construction of the core and of the tubular braided sheath may be varied within the range of variables describe above and according to other variables known to persons of skill in the art.

In one specialized embodiment the cord described in the above embodiments may be employed as a tension member wherein an outer diameter of the tension member is from about 0.04 mm to about 0.7 mm. In other embodiments, the tension member may have an outer diameter of about from about 0.04 mm to about 0.6 mm, or from about 0.04 mm to 0.5 mm. An exemplary tension member is a medical thread or suture.

In a further embodiment, the performance and characteristics of the cord may be modified and managed by application of finish compositions which are conventionally known to one of skill in the art. For example at least one of the core and/or the tubular braided sheath comprises a filament, fiber or strand having a coating of a cross-linked silicone polymer, or a non-cross-linked silicone polymer or a long chain fatty acid. An exemplary long chain fatty acid is stearic acid. Application of cross-linking silicone polymers to ropes of high performance polyethylene is described in U.S. Pat. No. 8,881,496B2.

Application of cross-linking silicone polymers, especially to the filaments and/or multifilaments contained in the strands of the tubular braided sheath and/or core may provide advantageous performance enhancement to the tensile strength managed cord structure of the present invention.

Generally, there are three crosslinking reaction methods available to prepare silicone resins: 1) peroxide cure wherein heat activation of polymerization occurs under the formation of peroxide free radicals; 2) condensation in the presence of a tin salt or titanium alkoxide catalyst under the influence of heat or moisture; and 3) addition reaction chemistry catalyzed by a platinum or rhodium complex which may be temperature- or photo-initiated.

Each of these systems are commercially available, from, for example, Dow Corning and are known to persons skilled in the art.

A cross-linked silicone coating may enhance moisture resistance of the of the strands and may also enhance the lubricity of the strands such that when the cord is under longitudinal stress the braid responds more efficiently in comparison to a non-coated device where frictional interaction may need to be overcome before the cinching effect is obtained.

The coating composition may be applied via surface application techniques which are known to those skilled in the art. These surface application techniques may include simple pumping finish solutions through a finish guide where the fiber comes into contact with the finish and is wicked into the fiber bundle via capillary action. Alternatively, other techniques may include spraying, rolling, or submersion application techniques such as dip coating. Subsequent treatment of the fiber with finish solution applied may include contact with roller or rollers for the purpose of setting the finish and/or influencing the degree of cross linking in a finish formulation. The roller(s) may or may not be heated. The coating composition may then be cured to cause cross-linking of the cross-linkable silicone polymer. When thermal curing is used the temperature may be from about 20° C., or from about 50° C., or from about 120° C., to about 200° C., or to about 170° C., or to about 150° C. The curing temperature and may be determined by the thermal stability properties of the filament, fiber or strand and the actual cross-linking system being employed.

The degree of the cross-linking obtained may be controlled to provide differing degrees of flexibility or other surface characteristics to the filament, fiber or strand. The degree of the cross-linking may be controlled by methods described by the cross-linking system suppliers and as known to persons skilled in the technology.

The degree of crosslinking may be determined by the method described in U.S. Pat. No. 8,881,496B2 where the coating is extracted with a solvent which dissolves monomer, but not the crosslinked polymer. The degree of cross-linking may be determined by the difference in weight before and after the extraction.

The degree of cross-linking may be at least about 20%, or at least about 30%, or at least about 50%, based on the total weight of the coating. The maximum degree of cross-linking may be about 100%.

The weight of the cross-linked coating may be from about 1 wt % to about 20 wt %, or to about 10 wt %, or to about 5 wt %, based on the total weight of the filament, fiber or strand.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

EXAMPLES

In the following examples, the sheath strands (yarns) were all of liquid crystalline polyester (LCP) available from Kuraray America Inc., Houston, TX The Vectran® HT grades used were 100 denier or 200 denier. The core also comprised 200, 400 or 1500 denier LCP yarns from Kuraray except for Example 6 where there was no core, Examples 10 and 11 comprised 1300 denier high molecular weight polyethylene (HMPE) Spectra® yarn from Honeywell Ltd. Example 12 was of para-aramid (PA) Kevlar® 49 yarn from Dow DuPont, Wilmington, DE The 1500 denier LCP yarn was 1550d/300f Vectran® HT 150 766-1 14A. The construction of the sheath and core components of the examples is summarized in Table 5. The number of braid carriers in all examples was four.

TABLE 5

| Example | Core Denier (d) and Twist (tpi) | Sheath Denier per Braid (d) and Pick Count (ppi) | Denier per Braid Carrier | Cord Break Tenacity (grams per denier) |
| --- | --- | --- | --- | --- |
| 1 | 400 d/0 tpi | 4 × 100 d/12 ppi | 100 | 24 |
| 2 | 400 d/2.5 tpi | 4 × 100 d/12 ppi | 100 | 27 |
| 3 | 400 d/0 tpi | 4 × 100 d/12 ppi | 100 | 27 |
| 4 | 200 d/6 tpi | 4 × 100 d/12 ppi | 100 | 26 |
| 5 | 400 d/6 tpi | 4 × 100 d/12 ppi | 100 | 25 |
| 6 | No Core | 4 × 100 d/6 ppi | 100 | 28 |
| 7 | 400 d/3 tpi | 4 × 200 d/12 ppi | 200 | 28 |
| 8 | 400 d/3 tpi | 4 × 200 d/12 ppi | 200 | 28 |
| 9 | 1500 d/3 tpi | 4 × 100 d/6 ppi | 100 | 28 |
| 10 | 1300 d HMPE/3 tpi | 4 × 100 d/6 ppi | 200 | 27 |

TABLE 5-continued

| Example | Core Denier (d) and Twist (tpi) | Sheath Denier per Braid (d) and Pick Count (ppi) | Denier per Braid Carrier | Cord Break Tenacity (grams per denier) |
|---|---|---|---|---|
| 11 | 1300 d HMPE/3 tpi | 4 × 100 d/12 ppi | 200 | 24 |
| 12 | 1500 d PA/3 tpi | 4 × 100 d/6 ppi | 200 | 17 |
| 13 | 400 d/3 tpi | 4 × 100 d/6 ppi | 100 | 26 | tpi = turns per inch of twist
ppi = sheath yarn count in picks per inch

Table 6 summarizes the estimate diameter of the core, the diameter of a single strand of the sheath and the external diameter of the finished cord. All dimensions are in micrometers.

TABLE 6

| | Example | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Core Diameter | 230 | 230 | 230 | 160 | 250 | 0 | 230 | 230 | 400 | 500 | 500 | 440 | 230 |
| Strand Diameter | 110 | 110 | 110 | 110 | 110 | 110 | 150 | 150 | 110 | 150 | 150 | 150 | 110 |
| Cord Diameter | 340 | 340 | 330 | 330 | 380 | 250 | 460 | 430 | 520 | 660 | 650 | 560 | 330 |

The invention claimed is:

1. A cord, comprising:
a tubular braided sheath comprising:
strands having an outer surface, an inner surface, and a central hollow portion defined by the inner surface and having a volume; and
a core within the central hollow portion of the tubular braided sheath;
wherein:
the strands each have a tensile strength of about 8 cN/dtex or more;
when the cord is in a relaxed state, the tubular braided sheath has a substantially cylindrical shape having an outer diameter of from about 20 μm to about 5 mm and a volume of the central hollow portion, wherein the core does not completely fill the volume of the central hollow portion of the tubular braided sheath in the relaxed state; and
when the cord is in a longitudinal tensioned state, the tubular braided sheath elongates under longitudinal tension such that a volume of at least a part of the central hollow portion of the tubular braided sheath in the longitudinal tensioned state is less than the volume in the relaxed state;
in the longitudinal tensioned state, the inner surface of the tubular braided sheath contacts and cinches a surface of the core such that slippage between the core and the tubular braided sheath is reduced, and
wherein the core occupies greater than about 95% of the volume of the central hollow portion of the tubular braided sheath in the relaxed state.

2. A cord, comprising:
a tubular braided sheath comprising:
strands having an outer surface, an inner surface, and a central hollow portion defined by the inner surface and having a volume; and
a core within the central hollow portion of the tubular braided sheath;
wherein:
the strands each have a tensile strength of about 8 cN/dtex or more;
when the cord is in a relaxed state, the tubular braided sheath has a substantially cylindrical shape having an outer diameter of from about 20 μm to about 5 mm and a volume of the central hollow portion, wherein the core does not completely fill the volume of the central hollow portion of the tubular braided sheath in the relaxed state; and
when the cord is in a longitudinal tensioned state, the tubular braided sheath elongates under longitudinal tension such that a volume of at least a part of the central hollow portion of the tubular braided sheath in the longitudinal tensioned state is less than the volume in the relaxed state;
in the longitudinal tensioned state, the inner surface of the tubular braided sheath contacts and cinches a surface of the core such that slippage between the core and the tubular braided sheath is reduced;
the strands of the tubular braided sheath comprise filaments selected from the group consisting of a liquid crystalline polyester filament, an aramid filament, co-polymer aramid filament, a polyether ether ketone filament, a poly(p-phenylene benzobisoxazole) filament, an ultra-high molecular weight polyethylene filament, a high modulus polyethylene filament, a polypropylene filament, a polyethylene terephthalate filament, a polyamide filament, a polyhydroquinone diimidazopyridine filament, a high-strength polyvinyl alcohol filament and combinations thereof, and
wherein the core occupies greater than about 95% of the volume of the central hollow portion of the tubular braided sheath in the relaxed state.

3. A cord, comprising:
a tubular braided sheath comprising:
strands having an outer surface, an inner surface, and a central hollow portion defined by the inner surface and having a volume; and
a core within the central hollow portion of the tubular braided sheath;
wherein:
the strands each have a tensile strength of about 8 cN/dtex or more;
when the cord is in a relaxed state, the tubular braided sheath has a substantially cylindrical shape having an outer diameter of from about 20 μm to about 5 mm and a volume of the central hollow portion, wherein the core does not completely fill the volume of the central hollow portion of the tubular braided sheath in the relaxed state; and
when the cord is in a longitudinal tensioned state, the tubular braided sheath elongates under longitudinal tension such that a volume of at least a part of the central hollow portion of the tubular braided sheath in the longitudinal tensioned state is less than the volume in the relaxed state;

in the longitudinal tensioned state, the inner surface of the tubular braided sheath contacts and cinches a surface of the core such that slippage between the core and the tubular braided sheath is reduced;

the core comprises one or more filaments selected from the group consisting of a liquid crystalline polyester filament, an aramid filament, co-polymer aramid filament, a polyether ether ketone filament, a poly(phenylene benzobisoxazole) filament, a polypropylene filament, a polyethylene terephthalate filament, a polyamide filament, a polyhydroquinone diimidazopyridine filament, and combinations thereof, and wherein the core occupies greater than about 95% of the volume of the central hollow portion of the tubular braided sheath in the relaxed state.

4. The cord according to claim 3, wherein a pick count of the braid of the tubular braided sheath in the relaxed state is from 30 to 3000 filament unit crossovers per meter.

5. The cord according to claim 3, wherein the core is twisted at a twist level of from greater than 0 up to 1600 turns per meter (tpm).

6. The cord according to claim 3, wherein the core is a braided core.

7. The cord according to claim 3 wherein, when in the relaxed state, a relationship between the sheath and core components of the cord conforms to the equation (I):

$$c/10 \leq p/t \leq (1.2 \cdot c) \quad (I),$$

wherein c is a strand count of the tubular braided sheath, p is a pick count per meter in the sheath, and t is a twist level of the core in turns per meter.

8. The cord according to claim 3, wherein a pick count of the tubular braided sheath in the longitudinal tensioned state is reduced in comparison to a pick count in the relaxed state.

9. The cord according to claim 3, wherein each strand of the tubular braided sheath is individually a twisted or untwisted monofilament.

10. The cord according to claim 3, wherein each strand of the tubular braided sheath is individually a twisted or untwisted multifilament.

11. The cord according to claim 10, wherein the strands of the tubular braided sheath comprise liquid crystalline polyester filaments and a content of the liquid crystalline polyester filaments is at least 50% by mass relative to a total mass of the tubular braided sheath.

12. The cord according to claim 3, wherein the tubular braided sheath is a combination of strands, wherein each strand is individually a twisted or untwisted monofilament or multifilament.

13. The cord according to claim 3, wherein the strands of the tubular braided sheath comprise filaments selected from the group consisting of a liquid crystalline polyester filament, an aramid filament, co-polymer aramid filament, a polyether ether ketone filament, a poly(p-phenylene benzobisoxazole) filament, an ultra-high molecular weight polyethylene filament, a high modulus polyethylene filament, a polypropylene filament, a polyethylene terephthalate filament, a polyamide filament, a polyhydroquinone diimidazopyridine filament, a high-strength polyvinyl alcohol filament and combinations thereof.

14. The cord according to claim 3, wherein the strands of the tubular braided sheath consist essentially of liquid crystalline polyester filaments.

15. The cord according to claim 3, wherein a strand count of the tubular braided sheath is from 4 to 24 ends.

16. The cord according to claim 3, wherein the core is a twisted or untwisted monofilament.

17. The cord according to claim 3, wherein the core is a twisted or untwisted multifilament.

18. The cord according to claim 3, wherein the core is a combination of strands, wherein each strand is individually a twisted or untwisted monofilament or multifilament.

19. The cord according to claim 3, wherein a mass ratio of a mass of the tubular braided sheath to a mass of the core per unit length of the cord is from about 95/5 to about 50/50.

* * * * *